(12) United States Patent
An et al.

(10) Patent No.: US 10,264,963 B2
(45) Date of Patent: Apr. 23, 2019

(54) METHODS FOR HIGH SENSITIVITY FLOW VISUALIZATION

(71) Applicants: Carl Zeiss Meditec, Inc., Dublin, CA (US); Carl Zeiss Meditec AG, Jena (DE)

(72) Inventors: Lin An, Walnut Creek, CA (US); Homayoun Bagherinia, Oakland, CA (US); Mary Durbin, San Francisco, CA (US); Vincent Michael Patella, Albany, CA (US)

(73) Assignees: CARL ZEISS MEDITEC, INC., Dublin, CA (US); CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 15/762,045

(22) PCT Filed: Sep. 22, 2016

(86) PCT No.: PCT/EP2016/072493
§ 371 (c)(1),
(2) Date: Mar. 21, 2018

(87) PCT Pub. No.: WO2017/050863
PCT Pub. Date: Mar. 30, 2017

(65) Prior Publication Data
US 2018/0256024 A1    Sep. 13, 2018

Related U.S. Application Data

(60) Provisional application No. 62/232,125, filed on Sep. 24, 2015.

(51) Int. Cl.
*A61B 3/10* (2006.01)
*G06T 7/254* (2017.01)
(Continued)

(52) U.S. Cl.
CPC .............. *A61B 3/102* (2013.01); *G06T 7/254* (2017.01); *G06T 11/008* (2013.01); *G06T 15/08* (2013.01);
(Continued)

(58) Field of Classification Search
CPC ........ G06T 7/254; G06T 11/008; G06T 15/08
See application file for complete search history.

(56) References Cited

U.S. PATENT DOCUMENTS

| 6,549,801 B1 | 4/2003 | Chen et al. |
| 7,301,644 B2 | 11/2007 | Knighton et al. |

(Continued)

FOREIGN PATENT DOCUMENTS

| EP | 2243420 A1 | 10/2010 |
| WO | 2010/030159 A2 | 3/2010 |

(Continued)

OTHER PUBLICATIONS

Al-Diri et al., "Automated Analysis of Retinal Vascular Network Connectivity", Computerized Medical Imaging and Graphics, vol. 34, 2010, pp. 462-470.

(Continued)

*Primary Examiner* — Edward Park
(74) *Attorney, Agent, or Firm* — Morrison & Foerster LLP

(57) ABSTRACT

Various systems and methods for improved OCT angiography imaging are described. An example method of identifying intraretinal fluid in optical coherence tomography (OCT) image data of an eye includes collecting OCT image data using an OCT system. The data includes at least one cluster scan containing OCT image data collected at approximately same set of locations on the sample. A first motion contrast image is generated by applying a first OCT angiography processing technique to the cluster scan to (Continued)

highlight motion contrast in the sample. A second motion contrast image is generated by applying a second OCT angiography processing technique to the cluster scan to highlight motion contrast in the sample. An image displaying intraretinal fluid in the eye is generated using the first and second motion contrast images and then displayed or stored or a further analysis thereof.

17 Claims, 4 Drawing Sheets

(51) Int. Cl.
    *G06T 11/00*     (2006.01)
    *G06T 15/08*     (2011.01)
(52) U.S. Cl.
    CPC ............ *G06T 2207/10101* (2013.01); *G06T 2207/30041* (2013.01); *G06T 2207/30104* (2013.01)

(56) References Cited

U.S. PATENT DOCUMENTS

| | | | |
|---|---|---|---|
| 7,359,062 | B2 | 4/2008 | Chen et al. |
| 7,854,510 | B2 | 12/2010 | Verdooner et al. |
| 8,079,711 | B2 | 12/2011 | Stetson et al. |
| 8,332,016 | B2 | 12/2012 | Stetson |
| 2003/0208326 | A1 | 11/2003 | Chen et al. |
| 2004/0076262 | A1 | 4/2004 | Shao et al. |
| 2005/0171438 | A1 | 8/2005 | Chen et al. |
| 2007/0019846 | A1 | 1/2007 | Bullitt et al. |
| 2007/0216909 | A1* | 9/2007 | Everett ............... A61B 5/0059 356/479 |
| 2008/0025570 | A1 | 1/2008 | Fingler et al. |
| 2008/0100612 | A1 | 5/2008 | Dastmalchi et al. |
| 2008/0159604 | A1 | 7/2008 | Wang et al. |
| 2008/0291463 | A1 | 11/2008 | Milner et al. |
| 2009/0005693 | A1 | 1/2009 | Brauner et al. |
| 2009/0268162 | A1 | 10/2009 | Stetson et al. |
| 2009/0270738 | A1 | 10/2009 | Izatt et al. |
| 2010/0027857 | A1 | 2/2010 | Wang |
| 2010/0113900 | A1 | 5/2010 | Shakespeare et al. |
| 2010/0159497 | A1 | 6/2010 | Kimia et al. |
| 2010/0189334 | A1 | 7/2010 | Tomidokoro et al. |
| 2010/0240986 | A1 | 9/2010 | Stiles |
| 2010/0245770 | A1 | 9/2010 | Zhang et al. |
| 2011/0034803 | A1 | 2/2011 | Stetson |
| 2011/0063573 | A1 | 3/2011 | Meyer et al. |
| 2011/0103657 | A1 | 5/2011 | Kang et al. |
| 2011/0109881 | A1 | 5/2011 | Munger et al. |
| 2011/0164791 | A1 | 7/2011 | Bajraszewski et al. |
| 2011/0169978 | A1 | 7/2011 | Lasser et al. |
| 2011/0243408 | A1 | 10/2011 | Takama |
| 2012/0035454 | A1 | 2/2012 | Tearney et al. |
| 2012/0053904 | A1 | 3/2012 | Yuasa et al. |
| 2012/0063665 | A1 | 3/2012 | Wang et al. |
| 2012/0075638 | A1 | 3/2012 | Rollins et al. |
| 2012/0120408 | A1 | 5/2012 | Yasuno et al. |
| 2012/0140171 | A1 | 6/2012 | Hirose et al. |
| 2012/0150029 | A1* | 6/2012 | Debuc .................. A61B 3/102 600/425 |
| 2012/0218517 | A1 | 8/2012 | Imamura |
| 2012/0274745 | A1 | 11/2012 | Russell |
| 2012/0277570 | A1 | 11/2012 | Todor et al. |
| 2012/0277579 | A1 | 11/2012 | Sharma et al. |
| 2012/0307014 | A1 | 12/2012 | Wang |
| 2013/0018254 | A1 | 1/2013 | Drucker |
| 2013/0094725 | A1 | 4/2013 | Gulsun et al. |
| 2013/0176532 | A1 | 7/2013 | Sharma et al. |
| 2013/0215235 | A1 | 8/2013 | Russell |
| 2013/0301008 | A1* | 11/2013 | Srivastava ......... G01B 9/02083 351/246 |
| 2014/0049632 | A1 | 2/2014 | Hemmer |
| 2014/0221827 | A1 | 8/2014 | Motaghiannezam et al. |
| 2014/0236002 | A1 | 8/2014 | Wang et al. |
| 2014/0293222 | A1 | 10/2014 | Coelho et al. |
| 2015/0168127 | A1 | 6/2015 | Takeno et al. |

FOREIGN PATENT DOCUMENTS

| | | |
|---|---|---|
| WO | 2010/129494 A2 | 11/2010 |
| WO | 2010/131944 A2 | 11/2010 |
| WO | 2010/138645 A2 | 12/2010 |
| WO | 2010/129494 A3 | 2/2011 |
| WO | 2011/097631 A2 | 8/2011 |
| WO | 2011/097631 A3 | 11/2011 |

OTHER PUBLICATIONS

An et al., "In Vivo Volumetric Imaging of Vascular Perfusion within Human Retina and Choroids with Optical Micro-Angiography", Optics Express, vol. 16, No. 15, Jul. 21, 2008, pp. 11438-11452.
An et al., "Noninvasive Imaging of Pulsatile Movements of the Optic Nerve Head in Normal Human Subjects using Phase-Sensitive Spectral Domain Optical Coherence Tomography", Optics Letters, vol. 38, No. 9, May 1, 2013, pp. 1512-1514.
An et al., "Optical Microangiography provides Correlation between Microstructure and Microvasculature of Optic Nerve Head in Human Subjects", Journal of Biomedical Optics, vol. 17, No. 11, Nov. 2012, pp. 116018-1-116018-6.
An et al., "Ultrahigh Sensitive Optical Microangiography for in Vivo Imaging of Microcirculations within Human Skin Tissue Beds", Optics Express, vol. 18, No. 8, Apr. 12, 2010, pp. 8220-8228.
Avakian et al., "Fractal Analysis of Region-based Vascular Change in the Normal and Non-Proliferative Diabetic Retina", Current Eye Research, vol. 24, No. 4, 2002, pp. 274-280.
Braaf et al., "Angiography of the Retina and the Choroid with Phase-Resolved OCT using Interval-Optimized Backstitched B-Scans", Optics Express, vol. 20, No. 18, Aug. 27, 2012, pp. 20516-20534.
Chang et al., "Glaucoma 2.0: Neuroprotection, Neuroregeneration, Neuroenhancement", Ophthalmology, vol. 119, No. 5, May 2012, pp. 979-986.
Chen et al., "Optical Doppler Tomography", IEEE Journal of Selected Topics in Quantum Electronics, vol. 5, No. 4, Jul./Aug. 1999, pp. 1134-1142.
Enfield et al., "In Vivo Imaging of the Microcirculation of the Volar Forearm using Correlation Mapping Optical Coherence Tomography (cmOCT)", Biomedical Optics Express, vol. 2, No. 5, May 1, 2011, pp. 1184-1193.
Final Office Action received for U.S. Appl. No. 13/781,375, dated Mar. 3, 2015, 14 pages.
Fingler et al., "Mobility and Transverse Flow Visualization using Phase Variance Contrast with Spectral Domain Optical Coherence Tomography", Optics Express, vol. 15, No. 20, Oct. 1, 2007, pp. 12636-12653.
Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.
Fung et al., "An Optical Coherence Tomography-Guided, Variable Dosing Regimen with Intravitreal Ranibizumab (Lucentis) for Neovascular Age-related Macular Degeneration", American Journal of Ophthalmology, vol. 143, No. 4, Apr. 2007, pp. 566-583.e2.
Ganesan et al., "Development of an Image-Based Network Model of Retinal Vasculature", Annals of Biomedical Engineering, vol. 38, No. 4, Apr. 2010, pp. 1566-1585.
Gaudric et al., "Optical Coherence Tomography in Group 2A Idiopathic Juxtafoveolar Retinal Telangiectasis", Arch Ophthalmol., vol. 124, Oct. 2006, pp. 1410-1419.
Herfkens, Robert, "Computational Visualization of 4D Cardiac Flow", Available at <https://web.archive.org/web/20110810120411/http://www.nvidia.com/object/quadro-fermi-video-view04.html>, Aug. 10, 2011, pp. 1-2.
Hong et al., "Multifunctional OCT Imaging of Macular Degeneration for Vasculature, RPE and Choroid Investigation", Investigative Ophthalmology & Visual Science, vol. 56, No. 5131, Jun. 2015, pp. 1-3.

(56) References Cited

OTHER PUBLICATIONS

International Preliminary Report on Patentability received for PCT Patent Application No. PCT/EP2013/059560, dated Nov. 20, 2014, 8 pages.
International Preliminary Report on Patentability received for PCT Patent Application No. PCT/EP2016/072493, dated Apr. 5, 2018, 9 pages.
International Search Report and Written Opinion received for PCT Patent Application No. PCT/EP2013/059560, dated Aug. 27, 2013, 9 pages.
International Search Report and Written Opinion received for PCT Patent Application No. PCT/EP2016/072493, dated Mar. 13, 2017, 13 pages.
Jia et al., "Optical Coherence Tomography Angiography of Optic Disc Perfusion in Glaucoma", Ophthalmology, vol. 121, No. 7, Jul. 2014, pp. 1322-1332.
Jia et al., "Quantitative OCT Angiography of Optic Nerve Head Blood Flow", Biomedical Optics Express, vol. 3, No. 12, Dec. 1, 2012, pp. 3127-3137.
Jia et al., "Split-Spectrum Amplitude-Decorrelation Angiography with Optical Coherence Tomography", Optics Express, vol. 20, No. 4, Feb. 13, 2012, pp. 4710-4725.
John et al., "Dimensions of the Foveal Avascular Zone using the Heidelberg Retinal Angiogram-2 in Normal Eyes", Indian Journal of Ophthalmology, vol. 59, No. 1, 2011, pp. 1-6.
Kim et al., "In Vivo Volumetric Imaging of Human Retinal Circulation with Phase-Variance Optical Coherence Tomography", Biomedical Optics Express, vol. 2, No. 6, Jun. 1, 2011, pp. 1504-1513.
Kim et al., "Noninvasive Imaging of the Foveal Avascular Zone with High-Speed, Phase-Variance Optical Coherence Tomography", Investigative Ophthalmology & Visual Science, vol. 53, No. 1, Jan. 2012, pp. 85-92.
Kirkpatrick et al., "OCT-Based Elastography for Large and Small Deformations", Optics Express, vol. 14, No. 24, Nov. 27, 2006, pp. 11585-11597.
Leitgeb et al., "Real-Time Assessment of Retinal Blood Flow with Ultrafast Acquisition by Color Doppler Fourier Domain Optical Coherence Tomography", Optics Express, vol. 11, No. 23, Nov. 17, 2003, pp. 3116-3121.
Leitgeb et al., "Ultrahigh Resolution Fourier Domain Optical Coherence Tomography", Optics Express, vol. 12, No. 10, May 17, 2004, pp. 2156-2165.
Leske, M. Cristina, "Open-Angle Glaucoma-An Epidemiologic Overview", Ophthalmic Epidemiology, vol. 14, Jul.-Aug. 2007, pp. 166-172.
Liu et al., "A Comparison of Doppler Optical Coherence Tomography Methods", Biomedical Optics Express, vol. 3, No. 10, Oct. 1, 2012, pp. 2669-2680.
Liu et al., "Intensity-Based Modified Doppler Variance Algorithm: Application to Phase Instable and Phase Stable Optical Coherence Tomography Systems", Optics Express, vol. 19, No. 12, Jun. 6, 2011, pp. 11429-11440.
Makita et al., "Comprehensive in Vivo Micro-Vascular Imaging of the Human Eye by Dual-Beam-Scan Doppler Optical Coherence Angiography", Optics Express, vol. 19, No. 2, Jan. 17, 2011, pp. 1271-1283.
Makita et al., "Optical Coherence Angiography for the Eye", SPIE, Jun. 10, 2009, pp. 1-3.
Makita et al., "Optical Coherence Angiography", Optics Express, vol. 14, No. 17, Aug. 21, 2006, pp. 7821-7840.
Mariampillai et al., "Optimized Speckle Variance OCT Imaging of Microvasculature", Optics Letters, vol. 35, No. 8, Apr. 15, 2010, pp. 1257-1259.
Mariampillai et al., "Speckle Variance Detection of Microvasculature using Swept-Source Optical Coherence Tomography", Optics Letters, vol. 33, No. 13, Jul. 1, 2008, pp. 1530-1532.
Massin et al., "Optical Coherence Tomography for Evaluating Diabetic Macular Edema Before and After Vitrectomy", American Journal of Ophthalmology, vol. 135, No. 2, Feb. 2003, pp. 169-177.

Melo et al., "Intravitreal Injection of Bevacizumab for Cystoid Macular Edema in Retinitis Pigmentosa", Acta Ophthalmologica Scandinavica, vol. 85, No. 4, 2007, pp. 461-463.
Motaghiannezam et al., "Logarithmic Intensity and Speckle-based Motion Contrast Methods for Human Retinal Vasculature Visualization using Swept Source Optical Coherence Tomography", Biomedical Optics Express, vol. 3, No. 3, Mar. 1, 2012, pp. 503-521.
Nam et al., "Complex Differential Variance Algorithm for Optical Coherence Tomography Angiography", Biomedical Optics Express, vol. 5, No. 11, Nov. 1, 2014, pp. 3822-3832.
Non-Final Office Action received for U.S. Appl. No. 13/543,373, dated Sep. 25, 2012, 9 pages.
Non-Final Office Action received for U.S. Appl. No. 13/781,375, dated Jun. 20, 2014, 18 pages.
Non-Final Office Action received for U.S. Appl. No. 13/854,623, dated Jan. 23, 2015, 8 pages.
Notice of Allowance received for U.S. Appl. No. 13/543,373, dated Jan. 2, 2013, 5 pages.
Notice of Allowance received for U.S. Appl. No. 13/854,623, dated Apr. 20, 2015, 9 pages.
Popovic et al., "Noninvasive Imaging of Human Foveal Capillary Network using Dual-Conjugate Adaptive Optics", Investigative Ophthalmology & Visual Science, vol. 52, No. 5, Apr. 2011, pp. 2649-2655.
Quigley et al., "The Mechanism of Optic Nerve Damage in Experimental Acute Intraocular Pressure Elevation", Investigative Ophthalmology & Visual Science, vol. 19, No. 5, May 1980, pp. 505-517.
Ramezani et al., "Agreement between Clinical Estimation and a New Quantitative Analysis by Photoshop Software in Fundus and Angiographic Image Variables", Int. Ophthalmol., vol. 29, Sep. 19, 2008, pp. 439-449.
Ren et al., "Cerebral Blood Flow Imaged with Ultrahigh-Resolution Optical Coherence Angiography and Doppler Tomography", Optics Letters, vol. 37, No. 8, Apr. 15, 2012, pp. 1388-1390.
Ren et al., "Real-Time in Vivo Blood-Flow Imaging by Moving-Scatterer-Sensitive Spectral-Domain Optical Doppler Tomography", Optics Letters, vol. 31, No. 7, Apr. 1, 2006, pp. 927-929.
Schmidt-Erfurth et al., "Three-Dimensional Topographic Angiography in Chorioretinal Vascular Disease", Investigative Ophthalmology & Visual Science, vol. 42, No. 10, Sep. 2001, pp. 2386-2394.
Schmitt, Joseph M., "OCT Elastography: Imaging Microscopic Deformation and Strain of Tissue", Optics Express, vol. 3, No. 6, Sep. 14, 1998, pp. 199-211.
Schmoll et al., "Imaging of the Parafoveal Capillary Network and its Integrity Analysis using Fractal Dimension", Biomedical Optics Express, vol. 2, No. 5, May 1, 2011, pp. 1159-1168.
Sibony et al., "Effects of Lowering Cerebrospinal Fluid Pressure on the Shape of the Peripapillary Retina in Intracranial Hypertension", Investigative Ophthalmology & Visual Science, vol. 55, No. 12, Dec. 2014, pp. 8223-8231.
Sigal et al., "Biomechanics of the Optic Nerve Head", Experimental Eye Research, vol. 88, 2009, pp. 799-807.
Spaide et al., "Fundus Autofluorescence and Central Serous Chorioretinopathy", Ophthalmology, vol. 112, No. 5, May 2005, pp. 825-833.
Srinivasan et al., "Rapid Volumetric Angiography of Cortical Microvasculature with Optical Coherence Tomography", Optics Letters, vol. 35, No. 1, Jan. 1, 2010, pp. 43-45.
Wang et al., "Depth-Resolved Imaging of Capillary Networks in Retina and Choroid using Ultrahigh Sensitive Optical Microangiography", Optics Letters, vol. 35, No. 9, May 1, 2010, pp. 1467-1469.
Wang et al., "Frequency Domain Phase-Resolved Optical Doppler and Doppler Variance Tomography", Optics Communications, vol. 242, 2004, pp. 345-350.
Wang et al., "Imaging Retinal Capillaries using Ultrahigh-Resolution Optical Coherence Tomography and Adaptive Optics", Investigative Ophthalmology & Visual Science, vol. 52, No. 9, Aug. 2011, pp. 6292-6299.
Wang et al., "Three Dimensional Optical Angiography", Optics Express, vol. 15, No. 7, Apr. 2, 2007, pp. 4083-4097.

(56) References Cited

OTHER PUBLICATIONS

White et al., "In Vivo Dynamic Human Retinal Blood Flow Imaging using Ultra-High-Speed Spectral Domain Optical Doppler Tomography", Optics Express, vol. 11, No. 25, Dec. 15, 2003, pp. 3490-3497.

Yazdanfar et al., "Imaging and Velocimetry of the Human Retinal Circulation with Color Doppler Optical Coherence Tomography", Optics Letters, vol. 25, No. 19, Oct. 1, 2000, pp. 1448-1450.

Zhao et al., "Doppler Standard Deviation Imaging for Clinical Monitoring of in Vivo Human Skin Blood Flow", Optics Letters, vol. 25, No. 18, Sep. 15, 2000, pp. 1358-1360.

Zhao et al., "Phase-Resolved Optical Coherence Tomography and Optical Doppler Tomography for Imaging Blood Flow in Human Skin with Fast Scanning Speed and High Velocity Sensitivity", Optics Letters, vol. 25, No. 2, Jan. 15, 2000, pp. 114-116.

Zheng et al., "Automated Segmentation of Foveal Avascular Zone in Fundus Fluorescein Angiography", Investigative Ophthalmology & Visual Science, vol. 51, No. 7, Jul. 2010, pp. 3653-3659.

Zotter et al., "Visualization of Microvasculature by Dual-Beam Phase-Resolved Doppler Optical Coherence Tomography", Optics Express, vol. 19, No. 2, 2011, pp. 1217-1227.

\* cited by examiner

METHODS FOR HIGH SENSITIVITY FLOW VISUALIZATION

PRIORITY

This application is a National Phase application under 35 U.S.C. § 371 of International Application No. PCT/EP2016/072493, filed Sep. 22, 2016, which in turn claims priority to U.S. Provisional Application Ser. No. 62/232,125, filed Sep. 24, 2015, the contents of both of which are hereby incorporated by reference.

FIELD OF THE INVENTION

The present application is directed to systems and methods for improved OCT angiography imaging, in particular high sensitivity imaging of motion and flow.

BACKGROUND

Optical coherence tomography (OCT) has become a valuable clinical imaging tool, since its introduction in 1991. OCT is based on an optical measurement technique known as low-coherence interferometry. OCT performs high resolution, cross-sectional imaging of internal microstructure of a physical object by directing a light beam to the physical object, and then measuring and analyzing magnitude and time delay of backscattered light. A cross-sectional image is generated by performing multiple axial measurements of time delay (axial scans or A-scans) and scanning the incident optical beam transversely. This produces a two-dimensional data set of A-scans (i.e. B-scans), which represents the optical backscattering in a cross-sectional plane through the physical object. Three-dimensional, volumetric data sets can be generated by acquiring sequential cross-sectional images by scanning the incident optical beam in a raster pattern (three-dimensional OCT (3D-OCT)). This technique yields internal microstructural images of the physical objects with very fine details. For example, pathology of a tissue can effectively be imaged in situ and in real time on the micron scale.

Several types of OCT systems and methods have been developed, for example, time-domain OCT (TD-OCT) and Fourier-domain OCT (FD-OCT). Use of FD-OCT enables high-resolution imaging of retinal morphology that is nearly comparable to histologic analysis. Examples of FD-OCT technologies include spectral-domain OCT (SD-OCT) and swept-source OCT (SS-OCT).

OCT may be used for identification of common retinovascular diseases, such as age-related macular degeneration (AMD), diabetic retinopathy (DR), and retinovascular occlusions.

However, despite the rapid evolution of OCT imaging, current OCT technology may not provide adequate visualization of retinal and choroidal microvasculature. Thus, clinicians are often compelled to order both OCT and fluorescein angiography (FA) in patients with retinovascular diseases. There has been an increased interest in using data generated during FD-OCT imaging to generate angiographic images of the fundus (OCT Angiography).

A variety of OCT Angiography techniques have been developed including but not limited to optical microangiography (OMAG), speckle variance, phase variance, correlation mapping, and decorrelation (see for example, US Patent Publication No. 2008/0025570; US Patent Publication No. 2010/0027857; US Patent Publication No. 2012/0307014; Fingler et al. "Mobility and transverse flow visualization using phase variance contrast with spectral domain optical coherence tomography" Opt. Express 2007, 15:12636-53; Mariampillai et al., "Speckle variance detection of microvasculature using swept-source optical coherence tomography", Optics Letters 33(13), 1530-1533, 2008; An et al., "In vivo volumetric imaging of vascular perfusion within human retina and choroids with optical micro-angiography," Opt. Express 16(15), 11438-11452, 2008; Enfield et al., "In vivo imaging of the microcirculation of the volar forearm using correlation mapping optical coherence tomography" (cmOCT), Biomed. Opt. Express 2(5), 1184-1193, 2011; and Jia et al. "Split-spectrum amplitude decorrelation angiography with optical coherence tomography" Optics Express 20(4) 4710-4725 (2012), the contents of all of which are hereby incorporated by reference). These techniques use the OCT data to achieve the imaging of functional vascular networks within microcirculatory tissue beds in vivo, without the use of exogenous contrast agents.

The key point of OCT angiography processing methods is to extract localized signal variations from the bulk motion signal of a background tissue by comparing OCT signals, such as B-scans, captured at different time points in the course of a single examination of an eye. Processing can be carried out on the complex OCT data (complex-based), the amplitude or intensity portion of the OCT data (intensity-based), or the phase portion of the data (phase-based). The separately processed intensity and phase information can also be combined in some approaches. Intensity-based approaches such as speckle variance, correlation mapping, and decorrelation, are easier to implement because of the reduced requirements for motion compensation and processing. They are also less sensitive to phase noise. However, intensity-based approaches have limitations in visualizing slower flows. Since the phase signal is more sensitive to the motion signal, phase-based approaches, such as phase variance, have much higher sensitivity to flow compared to the intensity-based approaches. But, approaches using only phase information can have increased error in measurements at low backscattered signal intensity. And, due to the higher flow sensitivity, phase-based OCT angiography methods also are able to detect very small motions in adjacent non-vascular tissue, for example, in the retinal nerve fiber layer. These motions commonly appear as artifacts in OCT angiograms.

It can therefore be advantageous to include both the amplitude and phase information in the OCT Angiography processing as in complex-based approaches. The biggest drawback to these types of approaches is the heavy computational load. With advances in parallel processing such as graphic processing units (GPUs), FPGAs, etc, the processing times required for complex optical coherence tomography angiography techniques becomes manageable. Several groups have proposed complex-based angiography processing techniques (see for example, US Patent Publication No. 2012/0277579 and US Patent Publication No. 2012/0307014, the contents of which are hereby incorporated by reference). Here we propose several additional complex-based OCT angiography processing approaches that in the past have only been applied to intensity data.

As mentioned, phase-based approaches can yield images with increased artifacts given their higher flow sensitivity. While tissue motion artifacts are not necessarily difficult to detect visually, they can limit the usefulness of the resulting images. Here we propose methods for removing artifacts through the use of two or more image analysis methods or imaging methods whose sensitivities to the artifact type in question differ.

Glaucoma refers to a group of eye diseases in which the optic nerve degenerates. Due to the degeneration of optic nerve fibers, glaucoma causes progressive, irreversible death of retinal ganglion cells, eventually leading to blindness. As the second leading cause of blindness, a number of parameters have been studied as possible causal factors in glaucoma (see for example, An, Lin, et al. "Noninvasive imaging of pulsatile movements of the optic nerve head in normal human subjects using phase-sensitive spectral domain optical coherence tomography." *Optics letters* 38.9 (2013): 1512-1514). Parameters include elevated intraocular pressure (IOP), low ocular perfusion pressure, increased scleral elasticity, age, ethnicity, myopia, local vascular abnormalities, and alterations in biomechanical properties of the optic nerve head (ONH) among others (see for example, Chang, Elma E., and Jeffrey L. Goldberg. "Glaucoma 2.0: neuroprotection, neuroregeneration, neuroenhancement." *Ophthalmology* 119.5 (2012): 979-986). However, the mechanism by which retinal ganglion cells are damaged in glaucoma remains controversial, presumably because individual patients demonstrate a wide range of sensitivities to these risk factors. For example, although elevated IOP has been considered as the primary risk factor for the development of glaucoma, it still cannot be used as a reliable indicator either of the glaucomatous status or likelihood of progressive ONH changes. Both ocular hypertensives (i.e., people with high IOP in the absence of glaucoma) and normal or low tension glaucoma (i.e., glaucoma with normal or low IOP) are common.

Evidence increasingly suggests that abnormal biomechanical properties of the ONH may play an important role in the development of glaucoma (see for example, Leske, M. Cristina. "Open-angle glaucoma an epidemiologic overview." *Ophthalmic epidemiology* 14.4 (2007): 166-172). Ganglion cell axons form into bundles and pass through pores in the lamina cribrosa of the ONH before exiting the eye. Pulsatile changes in IOP caused by blood flow might lead to pulsatile deformation of the tissues through which the blood flows. In the presence of abnormal ONH biomechanical properties, stress and strain resulting from pulse-induced motion could directly damage the retinal ganglion cells (see for example, Sigal, Ian A., and C. Ross Ethier. "Biomechanics of the optic nerve head." *Experimental eye research* 88.4 (2009): 799-807), disturb the capillary circulation perfusion of the retina nerve fiber layer (RNFL), or obstruct nutrient transport to (see for example, Quigley, Harry A., et al. "The mechanism of optic nerve damage in experimental acute intraocular pressure elevation." *Investigative ophthalmology & visual science* 19.5 (1980): 505-517) or cause chronic progressive deformation of ONH structures. In particular, the large arteries near the optic nerve head may deform the nerve head itself as well as the peripapillary RNFL tissue through which the arteries move to access the rest of the eye.

Characterization of pulse-induced axial RNFL movement in vivo would provide a valuable tool to evaluate RNFL biomechanical properties because such properties determine RNFL responses to IOP forces impinging on it. The extent to which ONH mechanical properties determine susceptibility to damage from IOP is unknown because functional measurement tools have been lacking. Pulse-induced movement of the RNFL offers one such tool, but no currently available technology is capable of measuring RNFL movement, probably because it is too small (typically a few micrometers).

Intraretinal or under retinal fluid spaces, have been detected in a plurality of retinal diseases, such as diabetic retinopathy, exudative age-related macular degeneration, or retinitis pigmentosa. Images of these spaces, captured by optical coherence tomography (OCT) have been reported in several research papers (see for example, Fung et al. "An optical coherence tomography-guided, variable dosing regimen with intravitreal ranibizumab (Lucentis) for neovascular age-related macular degeneration" Am J Ophthalmol. 2007, 143(4)566-583; Massin et al., Optical coherence tomography for evaluating diabetic macular edema before and after vitrectomy. Am J Ophthalmol. 2003, 135(2)169-177; Melo et al. "Intravitreal injection of bevacizumab for cystoid macular edema in retinitis pigmentosa" Acta Ophthalmol Scand. 2007, 85(4)461-463; and Gaudric et al. "Optical coherence tomography in group 2A idiopathic juxtafoveolar retinal telangiectasis" Arch Ophthalmol. 2006, 124(10)1410-1419, the contents of all of which are hereby incorporated by reference). The exact content of the spaces is unknown, but clinicians and scientists have attempted to investigate these spaces through the exhibited different optical properties made visible with OCT, which may help them to evaluate retinal diseases more thoroughly. For example, retreatment with ranibizumab for age-related exudative macular degeneration is dependent on whether the cysts are exudative or degenerative.

The motion properties of the fluid filled spaces have not been investigated yet due to the lack of appropriate examination tools. The motion properties may indicate whether the retinal fluid is active or not, helping the clinicians to make a correct diagnosis and establish better treatment strategies. Here we propose a technique that takes advantage of the different sensitivities of different motion contrast processing approaches to obtain more information on intraretinal fluid filled spaces.

SUMMARY

The present application is directed to systems and methods for improved OCT angiography imaging, in particular high sensitivity imaging of motion and flow. In a first embodiment, several new complex-based OCT angiography approaches are described wherein a traditionally intensity-based OCT angiography technique's sensitivity is improved by making it a complex-based technique. The techniques to which this is applied include correlation mapping optical coherence tomography (cmOCT), speckle variance, amplitude decorrelation, and complex difference after log.

Another embodiment of the present application is to improve the quality of ophthalmic image data by reducing image artifacts. In general, by comparing two or more images having differing sensitivity to unwanted artifacts, those artifacts can be identified, and then removed and/or replaced with non-artifactual images of the same tissue taken from some other relevant image. By applying two or more image analysis methods to the same image data, one of which is more sensitive to unwanted artifacts than the other, such artifacts can be identified, and then removed and/or replaced with non-artifactual images of the same tissue taken from some other relevant image. In a preferred embodiment, by comparing and combining OCT angiography images generated by phase related methods with intensity-based OCT angiograms, tissue motion artifacts can be identified, and then removed and/or replaced with non-artifactual images of the same tissue taken from some other relevant image. In addition, by comparing two OCT angiography data cubes captured at the same locations but along different fast scan orientations, tissue motion artifacts can be identified, and then removed and/or replaced with non-artifactual images of the same tissue taken from some other relevant image.

Another embodiment of the present application is directed towards characterizing the pulse-induced axial motion of the retinal nerve fiber layer (RNFL). In this embodiment, phase differences between repeated scans are analyzed to obtain the pulsatile motion of the nerve fiber layer. This pulsatile motion can be analyzed to obtain the health information of the nerve fiber layer which may relate to glaucoma.

In a further embodiment, the present application describes an approach to visualize the retinal fluid or leakage which contains moving scattering particles. This involves using a high sensitivity algorithm to detect all of the slow motion signals within the retina, using a lower sensitivity algorithm to detect faster motion signals within the retina, and comparing the slow motion signal with the fast motion signal to extract retinal Brownian motion signal. The detected slow motion signal could be used to represent abnormal slow flow regions, e.g. retinal fluid or leakage.

It should be noted that the embodiments described herein are not all-inclusive and many additional embodiments will be apparent to one of ordinary skill in the art in view of the figures and description. Moreover, it should be noted that the language used in the specification has been principally selected for readability and instructional purposes and not to limit the scope of the inventive subject matter.

The invention is described in the independent claims, suitable modifications are contained in the dependent claims and described hereafter.

BRIEF DESCRIPTION OF THE DRAWINGS

FIG. 2(a) shows a structural B-scan highlighting scattering fluid. FIG. 2(b) shows the OCT angiography image of the scattering fluid shown in FIG. 2(a) calculated with an intensity-based approach. FIG. 2(c) shows the OCT angiography signal of the scattering fluid shown in FIG. 2(a) calculated by replacing the intensity information in the intensity-based approach with complex signals.

FIG. 3(a) shows an en face vasculature image calculated with an intensity-based approach. FIG. 3(b) shows an en face vasculature image calculated with a complex-based approach.

FIG. 4(a) shows an en face vasculature image of a healthy retina with artifacts processed with a phase-related method. FIG. 4(b) shows an en face vasculature image of a healthy retina with artifacts processed with an intensity based method. FIG. 4(c) shows the artifact corrected image.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

The OCT system for collecting the data used in any of the embodiments discussed herein may comprise any type of OCT system. Examples of the OCT systems may include Time-domain OCT (TD-OCT) and Fourier-domain, or Frequency-domain OCT (FD-OCT). Examples of the FD-OCT may include spectral-domain OCT (SD-OCT), swept Source OCT (SS-OCT), and optical frequency domain Imaging (OFDI). The OCT technique can involve point scanning, line scanning, partial field scanning, or full field illumination of light on a sample.

Figure 1:
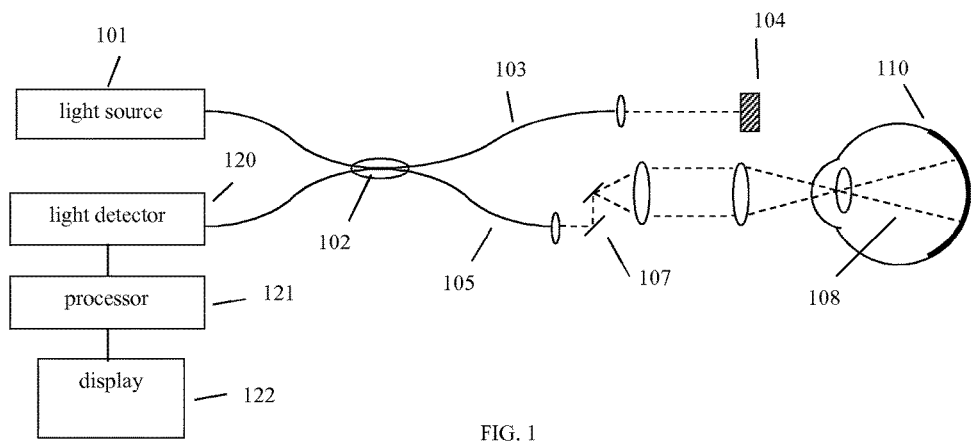
FIG. 1 is a generalized optical coherence tomography system.

A diagram of a generalized OCT system is shown in FIG. 1. Light from source 101 is routed, typically by optical fiber 105, to illuminate the sample 110, a typical sample being tissues in the human eye. The light source 101 can be either a broadband light source with short temporal coherence length in the case of SD-OCT or a wavelength tunable laser source in the case of SS-OCT. The light is scanned, typically with a scanner 107 between the output of the fiber 105 and the sample 110, so that the beam of light (dashed line 108) is scanned laterally (in x and y) over the area or volume to be imaged. Light scattered from the sample 110 is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector 120, those skilled in the art recognize that various designs of interferometers can be used for balanced or unbalanced detection of the interference signal. The output from the detector 120 is supplied to a processor 121. The results can be stored in the processor 121 or displayed on display 122. The processing and storing functions may be localized within the OCT instrument or functions may be performed on an external processing unit (such as the computer system 800 discussed herein in reference to FIG. 8) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire angiography data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for OCT angiography analysis including spot scanning, multi-spot scanning, partial field, and full field imaging systems. The techniques described herein could be applicable to any body parts, for example eye (both anterior and posterior chambers), skin, brain, muscle, cochlear, and internal organs if integrated with endoscope or catheter probe.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple A-scans or B-scans collected over time at approximately the same location(s) on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

The OCT system may use any one of a number of OCT Angiography processing algorithms on OCT data collected at the same or approximately the same transverse locations on a sample separated in time during a single patient examination to identify and/or visualize regions of motion or flow (see for example, US Patent Publication Nos. 2005/0171438, 2012/0307014, 2010/0027857, 2012/0277579; U.S. Pat. No. 6,549,801; Mariampillai et al., "Speckle variance detection of microvasculature using swept-source optical coherence tomography", Optics Letters 33(13), 1530-1533, 2008; Enfield et al., "In vivo imaging of the microcirculation of the volar forearm using correlation mapping optical coherence tomography" (cmOCT), Biomed. Opt. Express 2(5), 1184-1193, 2011; Nam et al. "Complex differential variance algorithm for optical coherence tomography angiography" Biomedical Optics Express 5(11) 3822-3832 2014; and Jia et al. "Split-spectrum amplitude decorrelation angiography with optical coherence tomography" Optics Express 20(4) 4710-4725 (2012)). As previously mentioned, motion contrast algorithms can be applied to the intensity information derived from the image data (intensity-based algorithm), the phase information from the image data (phase-based algorithm), or the complex image data (complex-based algorithm). An en face vasculature image is an image displaying motion contrast signal in which the data dimension corresponding to depth is displayed as a single representative value, typically by summing or integrating all or an isolated portion of the data (see for example, U.S. Pat. No. 7,301,644).

New Complex Processing Algorithms

The key point of OCT angiography is to extract the localized signal variations from the bulk motion signal of a background tissue by comparing OCT signals captured at different time points. Since the phase signal is more sensitive to the motion signal, phase-related methods, including both phase-based and complex-based approaches, have much higher flow sensitivity compared to intensity-based approaches. However, phase-based approaches can be more sensitive to noise when the system signal to noise ratio is low. Intensity-based approaches are easier to implement because of the reduced requirements for motion compensation. The only benefit in using intensity-based approaches is the processing speed. If the system has high computational power processor (e.g. GPUs), the processing speed will no longer be an issue. Therefore, we describe here using traditionally intensity-based approaches on complex OCT signals. In theory, any intensity-based approach can be transformed to being a complex-based approach after accurate phase compensation, which utilized average phase of the moving tissue to compensate the bulk motion (see for example, Makita, et al. "Optical coherence angiography," Opt. Express 14, 7821 (2006), and L. An and R. K. Wang, "In vivo volumetric imaging of vascular perfusion within human retina and choroids with optical micro-angiography,"

Opt. Express 16(15), 11438-11452 (2008)). The use of the full complex data will achieve much higher flow sensitivity and better image performance than the same approach using only the intensity portion of the OCT data. In order to utilize the complex information, the OCT angiography signal can be extracted using one of the following approaches previously used only on the intensity portion of the signal.

In correlation mapping optical coherence tomography (cmOCT), the following equation has been used to process the intensity of the OCT data (see for example, Enfield et al., "In vivo imaging of the microcirculation of the volar forearm using correlation mapping optical coherence tomography" (cmOCT), Biomed. Opt. Express 2(5), 1184-1193, 2011).

$$cmOCT(x, y) = \sum_{p=0}^{M}\sum_{q=0}^{N} \frac{[I_A(x+p, y+q) - \overline{I_A(x,y)}][I_B(x+p, y+q) - \overline{I_B(x,y)}]}{\sqrt{(I_A(x+p, y+q) - \overline{I_A(x,y)})^2 + I_B(x+p, y+q) - \overline{I_B(x,y)}}}$$

where $I_A$ and $I_B$ are the intensities of two frames captured in the same location at different times, M is the pixel along the z direction and N is the pixel number along the x direction. The resulting correlation map contains values on the range of 0±1 indicating weak and strong correlation respectively. By using the complex signal of the two frames $I_A$ and $I_B$ instead of the intensity, the approach becomes a complex-based technique with enhanced sensitivity compared to the intensity only approach.

Speckle variance (SV) is another intensity-based approach (see for example, Mariampillai et al. "Speckle variance detection of microvasculature using swept-source optical coherence tomography" Optics Letters 33(13) 1530-1532, 2008). In this approach, the motion contrast signal is calculated according to:

$$SV_{ijk} = \frac{1}{N}\sum_{i=1}^{N}\left[I_{ijk}(x, y) - \frac{1}{N}\sum_{i=1}^{N} I_{ijk}(x, y)\right]^2$$

$$= \frac{1}{N}\sum_{i=1}^{N}(I_{ijk} - I_{mean})^2$$

Where I is the intensity of a frame, j and k are the lateral and depth indices of the frame respectively, i is the frame index of one cluster and N is number of frames within one cluster. By using the complex signal instead of the intensity everywhere I appears in the equation, the approach becomes complex-based.

Amplitude decorrelation ($\overline{D}$), is another intensity-based approach (see for example, Jia et al. "Split-spectrum amplitude-decorrelation angiography with optical coherence tomography" Optics Express 20(4) 4710-4725, 2012) that can be converted to being a complex-based approach by replacing the intensity data for each frame, I, with the complex data according to the following equation:

$$\overline{D}(x, z) = 1 - \frac{1}{N-1}\sum_{n=1}^{N-1} \frac{I_n(x, z)I_{n+1}(x, z)}{\left[\frac{1}{2}I_n(x, z)^2 + \frac{1}{2}I_{n+1}(x, z)^2\right]}$$

where x, and z are the coordinates of pixels in x and z directions and n denotes the index of the B-scan in the total number of B-scans, N. This technique can be applied to the full spectrum or to different spectral bands of the signal.

Complex difference after log ($\overline{Dif}$) can be calculated according to:

$$\overline{Dif}(x, z) = 1 - \frac{1}{N-1}\sum_{n=1}^{N-1} |\log(|I_n(x, z)|)e^{-i\phi_n} - \log(|I_{n+1}(x, z)|)e^{-i\phi_{n+1}}|$$

where n is the index of a frame within a cluster, N is the total number of B-scans, φ is the phase of the frame. As in the other cases, the processing is carried out on I as the OCT complex signal instead of the intensity only signal traditionally used.

In order to demonstrate the improvement achieved by using a complex-based algorithm over an intensity-based approach, a flow phantom experiment was performed using a 68 KHz SD-OCT system. A phantom can be made of gelatin mixed with ~0.5% milk to simulate the background optical heterogeneity of the tissue that is well solidified to minimize the possible Brownian motion of particles in the background. A capillary tube with an inner diameter of ~400 μm is submerged in this background tissue and a syringe is used to pump a ~2% $TiO_2$ particle solution through it at the minimum required speed for each specified signal strength and z-motion speed. A stage moves the phantom with an oscillatory motion such that the mean speed is between 0.4 and 1 mm/s (for the tests below that specify a non-zero speed). A set of OCT images (20 B-frames scanned in the same location with 245 A-lines per B-frame) collected from the phantom are presented in FIGS. 2(a)-2(c).

Figures 2A, 2B, 2C:
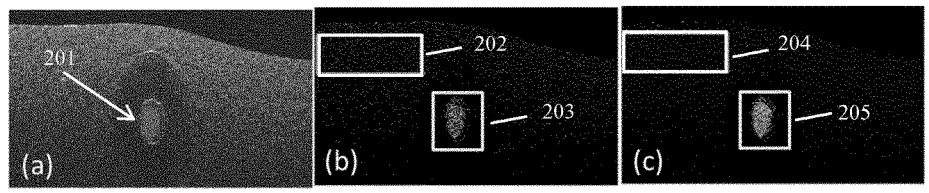
FIGS. 2(a)-2(c) illustrate the sensitivity improvement from using complex data in a traditionally intensity only analysis approach. In particular.

FIG. 2(a) shows an OCT micro structure B-scan image obtained using standard OCT image processing techniques. Scattering fluid (i.e., mimicking the blood cells in the blood vessels) is indicated with arrow 201. A plurality of these B-scans is obtained and analyzed to visualize flow using OCT Angiography processing algorithms. FIG. 2(b) shows the motion contrast (flow) signal generated from an intensity-based OCT angiography analysis approach. Box 202 indicates the background of the image while Box 203 highlights the flow signal.

Similarly, FIG. 2(c) shows the motion contrast information generated from a complex-based OCT angiography processing approach. Box 204 indicates the background level for this approach while Box 205 highlights the flow signal. Box 205 shows higher flow signal than Box 203 and Box 204 shows lower background than Box 202. For better comparison, the ratio between the signal integration within the signal and background squares were calculated for both the intensity-based and complex-based approaches. The complex approach has a ratio ~2.2 higher than the intensity only approach, which demonstrates that the complex approach has higher flow signal to noise ratio (SNR) compared to the intensity approach.

Figures 3A, 3B:
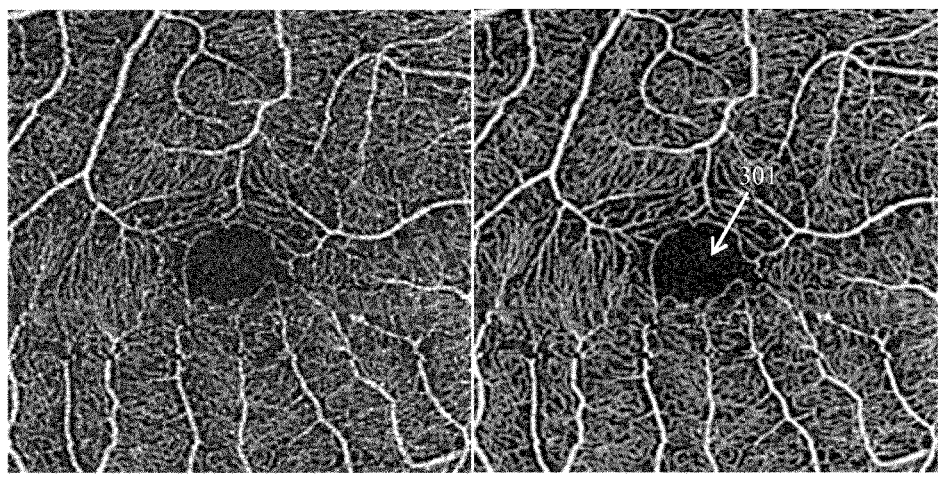
FIGS. 3(a) and 3(b) further illustrate the sensitivity improvement that comes from using complex data. In particular.

As another comparison, three dimensional OCT data captured from the eye of a normal subject was processed using both intensity-based and complex-based approaches. The results are demonstrated in FIGS. 3(a) and 3(b). Specifically, FIG. 3(a) is the intensity result and FIG. 3(b) is the complex result. Compared to FIG. 3(a), FIG. 3(b) shows better defined capillary networks and lower noise in the foveal avasculature zone (FAZ) area (301).

Artifact Removal

Phase-related angiography methods (including phase-based and complex-based methods) are more sensitive to small motions of blood in the vasculature and thus have potential to produce higher flow sensitivity angiograms for capillaries. However, due to the higher flow sensitivity, phase-related OCT angiography methods also detect very small motions in adjacent non-vascular tissue, for example, in retinal nerve fiber layer, and these motions commonly appear as artifacts in OCT angiograms.

Here we describe two methods for removing and replacing areas of OCT angiography images containing motion artifacts. The first method uses the differences between phase-related and intensity-based OCT angiography images. Because the tissue motion is very slow, it can be detected by the phase-related methods but cannot be detected by the intensity-based OCT angiography approaches. In order to identify the tissue motion artifact regions, images generated using a phase-related processing algorithm can be compared to images generated using an intensity-based processing algorithm. The region where the flow contrast value is significantly higher in the flow image processed by the phase-related algorithm is the tissue motion region. By setting a threshold (e.g. the value processed by a phase-related algorithm is 2 times higher than the value processed by intensity-based algorithm), the tissue motion region could be extracted. Then, regions of tissue motion artifact in phase-related angiograms can be replaced by the same regions of angiography images generated by the intensity-based analysis, or by the corresponding image area generated by some other method. Comparisons of phase-related and intensity-based analyses can be performed either using the very same OCT image or image set, or on separately-acquired image data acquisitions. Adjustments can be made to the image brightness to make the replacement sections blend in with the original image.

The second method is to capture two sets of OCT data of the same tissue suitable for OCT angiography processing, but with different imaging conditions, one exemplary embodiment being where the two data sets have orthogonal, fast scan directions. For example, the first set of image data might be taken by scanning the sample horizontally and the second set of image data by scanning the sample vertically. Both cubes may be processed by the phase related algorithm. The appearance of tissue motion artifacts in the processed image data depends upon the scan direction, but the appearance of the vasculature does not, or at least it depends much less on the scan direction. By comparing the two processed data cubes and extracting the same vasculature pattern from the two sets of image data, the difference between two vasculature images can be identified as the tissue motion artifacts which can be removed directly. The two sets of image data may be acquired in immediate succession or may be separated substantially in time. The artifact locations seen in the image generated from the data scanned in one direction can be replaced by the corresponding area in the image data set collected by scanning in the orthogonal scan direction if that area is unaffected by tissue motion. If both data sets are affected with artifacts in the same areas, but affected in different ways, it is still possible to identify and excise the affected areas. The artifact affected area could be replaced with an image generated from an intensity-based processing technique or from a phase-related image taken at yet a third scanning angle.

Figures 4A, 4B, 4C:
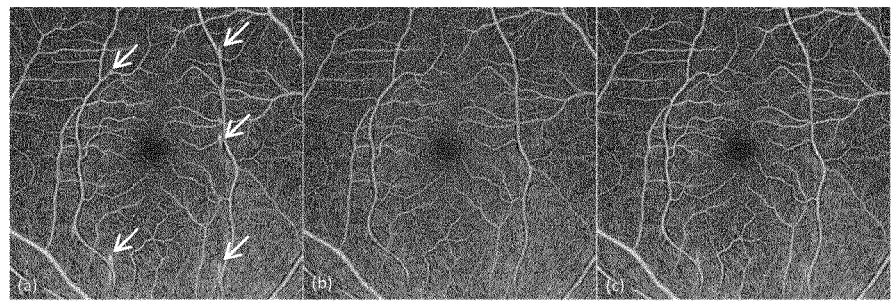
FIGS. 4(a)-4(c) illustrate the improvement in imaging made possible by the artifact reduction approach of one embodiment of the present application. In particular.

Image results before and after tissue motion artifact removal using the first artifact removal approach are demonstrated in FIGS. 4(a)-4(c). Specifically, FIG. 4(a) is the vasculature map generated by a phase-related method. The image provides visualization of the capillary network. However, the map also shows several vertical artifacts which are generated by tissue motion indicated by the arrows. FIG. 4(b) is the intensity based vasculature map. Compared to FIG. 4(a), the intensity based vasculature image has no NFL motion artifacts but has much higher noise level. FIG. 4(c) is the vasculature map after the artifact removal process. Compared to FIG. 4(a), the vertical tissue motion artifacts are clearly removed, while the vasculature is not affected.

The first artifact removal approach can be achieved by analyzing the same image data twice, and thus may have the advantage that it requires fewer images than the second approach. However, it involves substituting parts of the intensity-based angiography image into areas of the phase-related angiography image that contain artifacts. Intensity-based angiography images are frequently inferior to phase-related images. Thus, this method of artifact correction may sometimes show areas of degraded resolution where artifacts used to be.

The second artifact removal approach requires comparison of at least two different images, and thus image acquisition may take longer and there may be more data to analyze, archive and later access. On the other hand, the two images might then be averaged to produce an overall image having a better signal to noise (S/N) ratio. Finally, it may be that most or all of the artifact ridden areas in one image do not overlap with areas of artifacts in the second image, in which case, in aggregate, there would be a complete and artifact-free phase-sensitive angiogram, and it would not be necessary to use parts of the intensity-based image to patch the phase-sensitive image.

So far the use of these artifact removal approaches has focused on the removal of artifacts from Optical Coherence Tomography (OCT) Angiography images, when such artifacts have been generated by motion other than blood flow. This approach can remove OCT angiographic image artifacts associated with motion of the Retinal Nerve Fiber, presumably caused by the cardiac pulse. Tissue motion that is presumably caused by the cardiac pulse is commonly seen in the Retinal Nerve Fiber Layer (RNFL) during OCT angiography, but might also be present in other tissues of the eye and indeed in other parts of the body. For instance, in OCT angiography of the brain, motion artifacts might be observed in a completely different tissue, e.g. the cerebral cortex. Such motion is thought to be commonly associated with variations in blood pressure associated with the heartbeat, but may also have other causes, such as environmentally-imposed vibrations. The present approaches could be applied to these types of imaging.

More generally, the methods might be applied to removing unwanted motion artifacts from non-angiographic OCT applications that are sensitive to, or attempt to, detect and/or quantify motion in the body. One example would be the mapping of the lymph system throughout the body, or perhaps mapping of the nervous system with methods that are sensitive to retrograde axoplasmic transport.

The approaches may also make it possible to isolate image areas of tissue motion associated with the cardiac pulse, by removing all parts of the image that are not associated with the cardiac pulse. An example of this might be the suggestions of Murray A. Johnstone & Ruikang K. Wang that phase-sensitive OCT images might be used to assess how normally or abnormally the trabecular meshwork and Schlemm's canal are moving in response to the cardiac pulse (see for example, US Patent Publication No. 2014/0236002). Similar to nerve fiber motion, the trabecular meshwork and Schlemm's canal motion are very slow, so can only be detected by phase-related approaches. Using the same artifact removal methods that were discussed above, they could be extracted automatically.

RNFL Layer Motion Detection

In addition to removing artifacts resulting from tissue motion, OCT Angiography techniques can be used to characterize pulse-induced tissue motion, such as that of the retinal nerve fiber layer (RNFL). Accurate measurements of nerve fiber layer motions may provide more accurate information to access its health, which can be used for Glaucoma diagnosis.

Recent studies have demonstrated OCT-based phase measurements to be sensitive to slow motion of blood within capillaries. Such sensitivity might be usefully applied to measure the small movements of the RNFL in response to the blood flow. In order to detect the RNFL motion, a regular OCT system as illustrated in FIG. 1 could be used to repeatedly scan over one location on an eye during a patient visit. By calculating the phase difference between adjacent frames, the velocity of the RNFL could be detected. By repeatedly scanning B-scans at a frequency of (e.g. 200 frames/second) over the same location for a couple of seconds, the pulsatile motion pattern of the nerve fiber layer could be detected and sampled over a time period associated with the heartbeat. Further analysis of the pulsatile pattern, including the motion amplitude, the velocity amplitude, or the pulsatile frequency could be used to provide information about the NFL status. Measurements on normal eyes and eyes with glaucoma may indicate measurable differences in these populations.

Figures 5A, 5B:
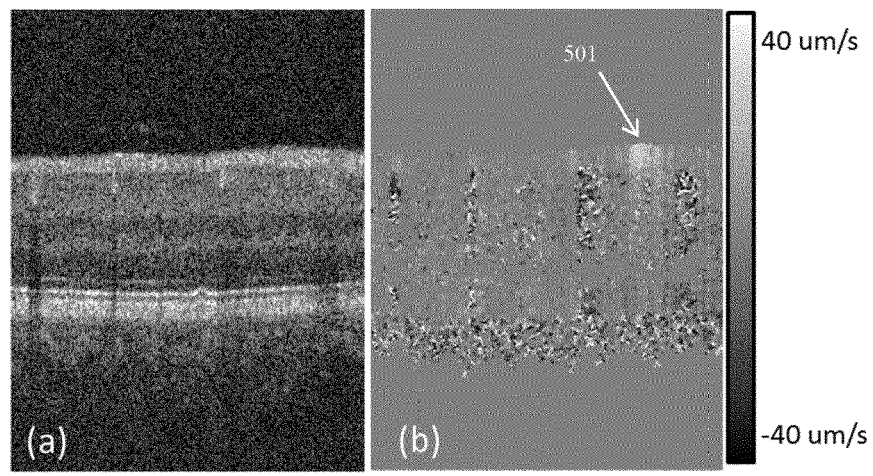
FIG. 5(a) is a standard structural cross sectional B-scan image of the eye.
FIG. 5(b) shows the bi-directional velocity map generated by comparing the phase information in four repeated B-scans.

The results of such an approach are demonstrated in FIGS. 5(a) and 5(b). In particular, FIG. 5(a) shows a standard structural B-scan of the eye. FIG. 5(b) shows the bi-directional velocity map generated by comparing the phase information in a cluster of four repeated B-scans. The image is shown in gray scale where white is used to indicate that the tissue is moving towards the incident measurement beam at 40 um/sec and black indicates that the tissue is moving away from the incident measurement beam at 40 um/sec. The horizontal columns of speckled black and white represent blood vessels. There is a bright signal, 501, in the RNFL adjacent to the largest of these vessels. This signal is likely related to pulsatile motion of the RNFL in response to flow through the artery at the time the B-scan was acquired.

B-scans that deliberately sample this signal at times and locations designed to optimize the measurement including, but not limited to, full-field OCT or faster measurement speeds, would be helpful. Special scan patterns might be designed to optimize visualization of tissue flow or motion instead of blood flow within vessels. At current measurement speeds (e.g., 27-70 KHz), scan patterns to support this measurement might include line scans or radial scans that are parallel to the major arteries, or circular or other scans that are perpendicular to them. Such scan patterns could be designed to be parallel to or orthogonal to the expected direction of tissue motion to optimize detection, and to have a frequency or separation of B-scans that has timing optimized to capture the flow. The scans might avoid volume imaging in favor of detection at a particular location so that biomechanics could be imaged dynamically. Circular scans might be performed fast enough to allow gating of the flow signal, so that motion associated with different phases of the heartbeat might be more effectively measured. Gating the acquisition so that detection can be matched to the heartbeat or breathing could allow subtle tissue motion associated with these physiological motions to be collected and averaged to increase sensitivity, and to associate the visualized or measured flow with the cardiac or respiration cycle. This approach could also be used to measure the motion and biodynamics of other highly scattering ocular tissues such as the trabecular meshwork, Schlemm's canal, lamina cribrosa, sclera, Bruch's membrane, or RPE. Biodynamics of the RPE or Bruch's membrane in the vicinity of the optic disc may be of interest in papilledema as well as glaucoma and other optic neuropathies, since it has been shown that the shape of the RPE may be affected by these pathologies (see for example, Sibony et al. "Effects of lowering cerebrospinal fluid pressure on the shape of the peripapillary retina in intracranial hypertension" Invest Ophthalmol Vis Sci. 2014 Nov. 18; 55(12):8223-31)

Fluid Detection

The motion properties of intraretinal or under retinal fluid spaces may provide valuable information to clinicians on the fluid status useful in diagnosing and treating diseases. Here we describe how two motion contrast imaging algorithms with different flow sensitivities (one with higher flow sensitivity and one with lower flow sensitivity) can be applied to the data captured from a patient to isolate the moving fluid signal from the motion contrast images. In order to generate a 2D fluid map, first B-scan cross sectional flow contrast images are generated using both a high flow sensitivity algorithm and a low flow sensitivity algorithm. The regions having higher values in the image processed by the high flow sensitivity algorithm are generated from slow flow. The images generated by the two different algorithms are compared to generate a difference image (e.g. by subtracting the low flow sensitivity B-scan flow contrast image from the high flow sensitivity B-scan flow contrast image). The image generation and comparison steps are repeated for all the OCT data in a three dimensional volume. Then, all the difference images resulting from the 3D data cube are combined into a stack and the flow contrast differences can be integrated between two retinal layers (e.g. the ILM and the RPE), to generate a 2D fluid map.

Figures 6A, 6B, 6C, 6D:
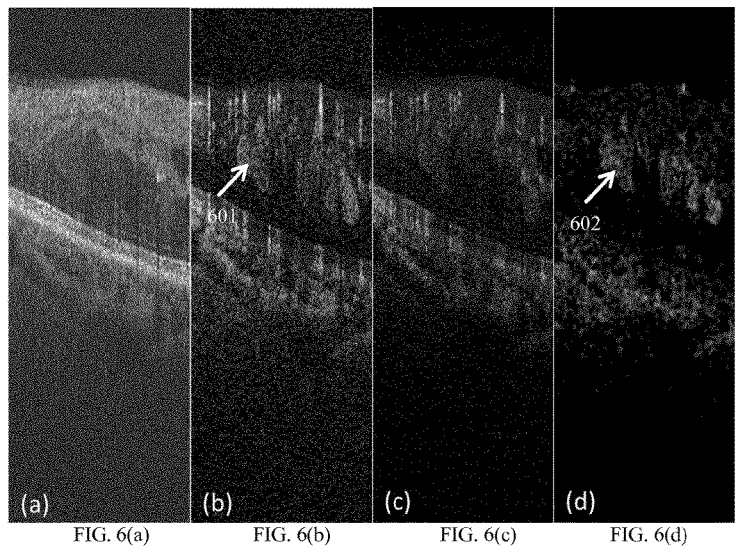
FIG. 6(a) is the regular cross sectional B-scan image of an eye.
FIG. 6(b) is the corresponding motion contrast image obtained by applying a high flow sensitivity algorithm to the OCT image data.
FIG. 6(c) is the corresponding motion contrast image obtained from applying a low sensitivity algorithm to the OCT data.
FIG. 6(d) is the difference image obtained by subtracting FIG. 6(c) from FIG. 6(b).

Results of this approach are demonstrated in FIGS. 6(a)-6(d). FIG. 6(a) is the regular cross sectional B-scan image of an eye collected with a 67 KHz SD-OCT system. FIG. 6(b) is the corresponding motion contrast image obtained by applying a high flow sensitivity algorithm to the OCT image data, in this case, a complex-based algorithm. FIG. 6(c) is the corresponding motion contrast image obtained from applying a low sensitivity algorithm to the OCT image data, in this case, an intensity-based OCT angiography algorithm. Because the moving velocity of retinal fluid (Brownian motion) is relatively slow compared to the blood flow, it can detected by the high flow sensitivity image but not in the low flow sensitivity image. FIG. 6(b) demonstrates more motion signals as indicated by arrow 601. FIG. 6(d) is the difference image obtained by subtracting FIG. 6(c) from FIG. 6(b). The arrow 602 points at the fluid signal.

Figures 7A, 7B, 7C, 7D:
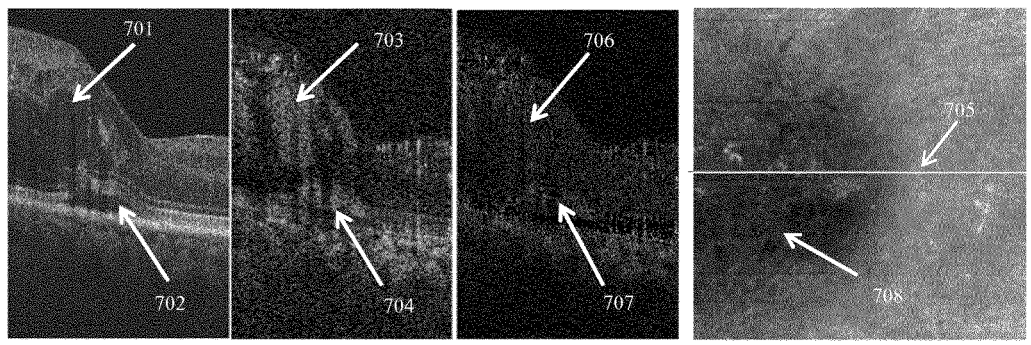
FIG. 7(a) shows a structural B-scan through the fovea.
FIG. 7(b) is the corresponding flow contrast image generated by a high sensitivity flow contrast algorithm for that B-scan location.
FIG. 7(c) is the flow contrast image generated by a low sensitivity flow contrast algorithm.
FIG. 7(d) is the mean intensity en face image generated by averaging the structure pixels between two layers (in this case between ILM and RPE).
Figures 7E, 7F, 7G:
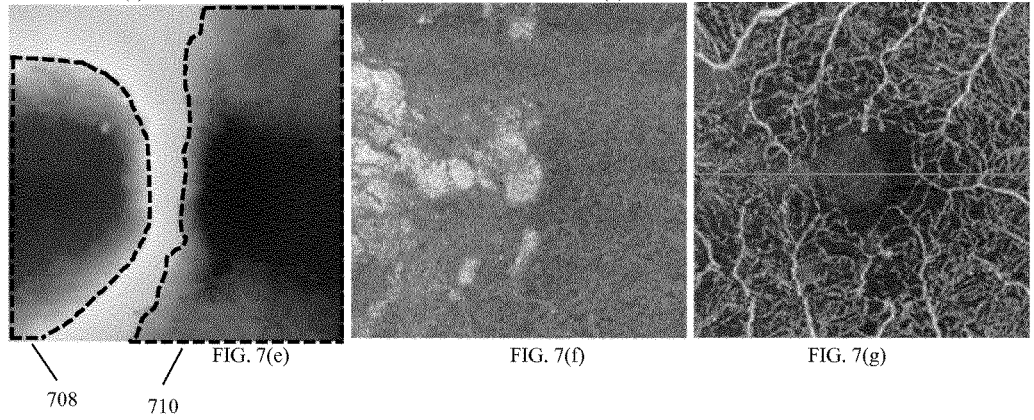
FIG. 7(e) is a map showing the thickness between the RPE and the ILM.
FIG. 7(f) shows the result of subtracting the high sensitivity flow contrast map from the low sensitivity flow contrast map.
FIG. 7(g) shows the vasculature map resulting from a complex-based OCT angiography processing.

The phase-related and intensity-based processing and difference image generation can be repeated over a range of transverse locations on the sample. The results are demonstrated in FIGS. 7(a)-7(g). FIG. 7(a) shows a structural B-scan through the fovea. Locations 701 and 702 are two areas of hyporeflectivity, consistent with the presence of cystic fluid in this eye with diabetic retinopathy. FIG. 7(b) is the corresponding flow contrast image generated by the high sensitivity flow contrast algorithm for that B-scan location. The two areas of hyporeflectivity (i.e., locations 703 and 704) in FIG. 7(b) show a strong motion signal indicating the presence of Brownian motion within the cystic space. The high sensitivity flow contrast images determined for all locations across the imaged area are combined to yield a high sensitivity flow contrast map. FIG. 7(c) is the flow contrast image generated by the low sensitivity flow contrast algorithm. The low sensitivity flow contrast images determined for all locations across the imaged area are combined to yield a low sensitivity flow contrast map. FIG. 7(d) is the mean intensity en face image generated by averaging the structure pixels between two layers (in this case between ILM and RPE). Line 705 indicates the location of the B-scan in FIGS. 7(a) and 7(b). Location 706 in FIG. 7(c) corresponds to location 701 in the B-scan (FIG. 7(a)), and location 707 in FIG. 7(c) corresponds to location 702 in the B-scan (FIG. 7(a)). Compared to locations 703 and 704 in FIG. 7 (b), 706 and 707 show much weaker signal which indicates that the fluid signal is very slow and cannot be detected by an intensity based algorithm. The hyporeflective area 708 to the left (FIG. 7(d)) is caused by the edema. FIG. 7(e) is a map showing the thickness between the RPE and the ILM, with reference numeral 708 representing the thicker areas and reference numeral 710 representing the thinner areas. The large area 708 is consistent with thickening due to the edema. In a preferred embodiment, FIG. 7(e) is a color-coded map where different colors can be used to represent the thicker and thinner areas. For example, the left portion 708 may be color-coded in red to represent the thicker areas and the right portion 710 may be color-coded in blue to represent the thinner areas. FIG. 7(f) shows the result of subtracting the high sensitivity flow contrast map from the low sensitivity flow contrast map, which clearly indicates those areas of fluid that have slow, Brownian motion within them. FIG. 7(g) shows the vasculature map resulting from a complex-based OCT angiography processing that contains both the rapid flow in the retinal vessels as well as the slow Brownian flow in the cysts.

The methods disclosed above may be used for any OCT related application. For example, the methods may be used in forming larger field of view OCT images of the sample. The OCT system disclosed above (i.e., with respect to FIG. 1) may provide any information related to the sample. For example, this system, which may use the methods disclosed herein, may provide 2D (i.e. cross-sectional) images, en-face images, 3-D images, metrics related to a health condition, and the like. This system may be used with any other system. For example, the OCT system may be used with a surgical system or surgical microscope system for diagnostic or treatment purposes. The OCT system may be used to analyze any sample. For example, the OCT system may be used in analysis, e.g. formation of images, of, for example, any type of life forms and inanimate objects. Examples of life forms may be animals, plants, cells or the like.

Figure 8:
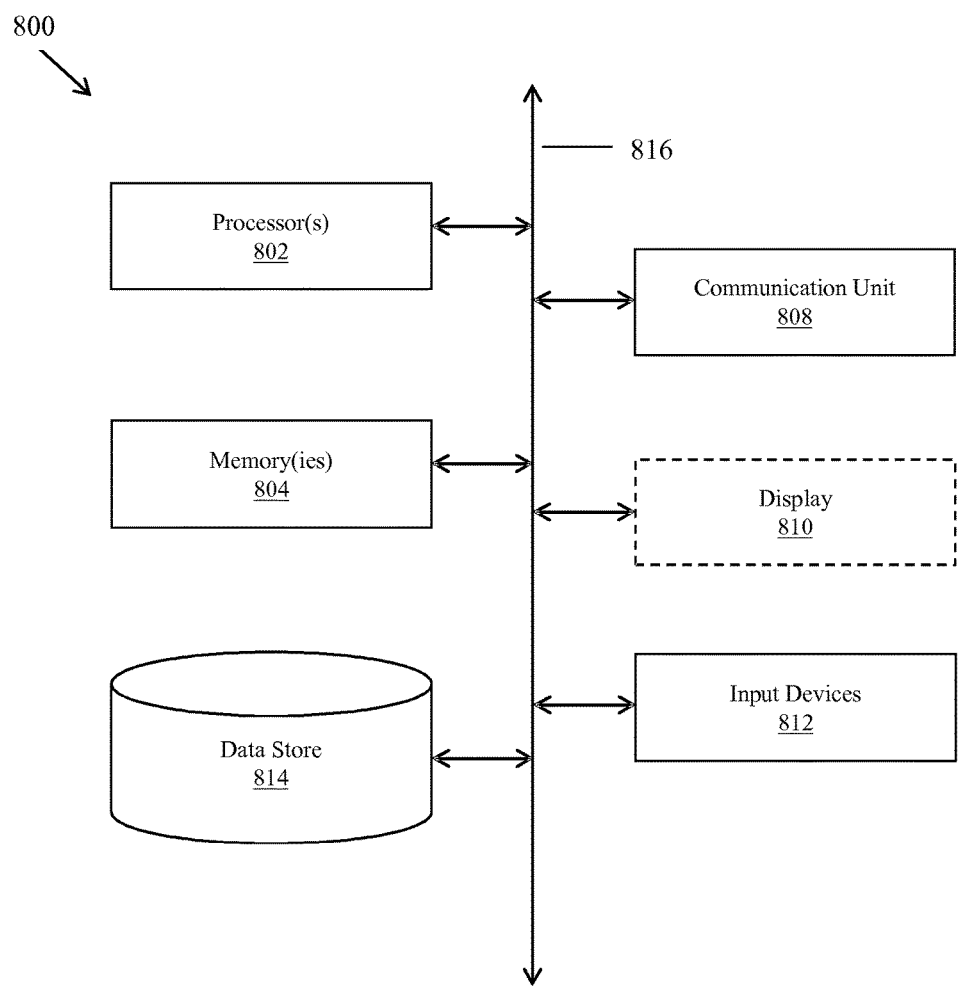
FIG. 8 is a block diagram of a general computer system that may perform the functions discussed in this disclosure according to one aspect of the present invention.

Unless otherwise indicated, the processing unit 121 that has been discussed herein (e.g., in reference to FIG. 1) may be implemented with a computer system configured to perform the functions that have been described herein for this unit. For instance, the processing unit 121 can be implemented with the computer system 800, as shown in FIG. 8. The computer system 800 may include one or more processors 802, one or more memories 804, a communication unit 808, an optional display 810, one or more input devices 812, and a data store 814. The display 810 is shown with dotted lines to indicate it is an optional component, which, in some instances, may not be a part of the computer system 800. In some embodiments, the display 810 discussed herein is the display 122 that has been discussed herein in reference to FIG. 1.

The components 802, 804, 808, 810, 812, and 814 are communicatively coupled via a communication or system bus 816. The bus 816 can include a conventional communication bus for transferring data between components of a computing device or between computing devices. It should be understood that the computing system 800 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 802 may execute various hardware and/or software logic, such as software instructions, by performing various input/output, logical, and/or mathematical operations. The processor(s) 802 may have various computing architectures to process data signals including, for example, a complex instruction set computer (CISC) architecture, a reduced instruction set computer (RISC) architecture, and/or architecture implementing a combination of instruction sets. The processor(s) 802 may be physical and/or virtual, and may include a single core or plurality of processing units and/or cores. In some embodiments, the processor(s) 802 may be capable of generating and providing electronic display signals to a display device, such as the display 810, supporting the display of images, capturing and transmitting images, performing complex tasks including various types of feature extraction and sampling, etc. In some embodiments, the processor(s) 802 may be coupled to the memory(ies) 804 via a data/communication bus to access data and instructions therefrom and store data therein. The bus 816 may couple the processor(s) 802 to the other components of the computer system 800, for example, the memory(ies) 804, the communication unit 808, or the data store 814.

The memory(ies) 804 may store instructions and/or data that may be executed by the processor(s) 802. In some embodiments, the memory(ies) 804 may also be capable of storing other instructions and data including, for example, an operating system, hardware drivers, other software applications, databases, etc. The memory(ies) 804 are coupled to the bus 816 for communication with the processor(s) 802 and other components of the computer system 800. The memory(ies) 804 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 802. A non-transitory computer-usable storage medium may include any and/or all computer-usable storage media. In some embodiments, the memory(ies) 804 may include volatile memory, non-volatile memory, or both. For example, the memory(ies) 804 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 121 may include one or more computers or processing units at the same or different locations. When at different locations, the computers may be configured to communicate with one another through a wired and/or wireless network communication system, such as the communication unit 808. The communication unit 808 may include network interface devices (I/F) for wired and wireless connectivity. For example, the communication unit 808 may include a CAT-type interface, USB interface, or SD interface, transceivers for sending and receiving signals using Wi-Fi™; Bluetooth®, or cellular communications for wireless communication, etc. The communication unit 808 can link the processor(s) 802 to a computer network that may in turn be coupled to other processing systems.

The display 810 represents any device equipped to display electronic images and data as described herein. The display 810 may be any of a conventional display device, monitor or screen, such as an organic light-emitting diode (OLED) display, a liquid crystal display (LCD). In some embodiments, the display 810 is a touch-screen display capable of receiving input from one or more fingers of a user. For example, the device 810 may be a capacitive touch-screen display capable of detecting and interpreting multiple points of contact with the display surface.

The input device(s) 812 are any devices for inputting data on the computer system 800. In some embodiments, an input device is a touch-screen display capable of receiving input from one or more fingers of the user. The functionality of the input device(s) 812 and the display 810 may be integrated, and a user of the computer system 800 may interact with the system by contacting a surface of the display 810 using one or more fingers. In other embodiments, an input device is a separate peripheral device or combination of devices. For example, the input device(s) 812 may include a keyboard (e.g., a QWERTY keyboard) and a pointing device (e.g., a mouse or touchpad). The input device(s) 812 may also include a microphone, a web camera, or other similar audio or video capture devices.

The data store 814 can be an information source capable of storing and providing access to data. In the depicted embodiment, the data store 814 is coupled for communication with the components 802, 804, 808, 810, and 812 of the computer system 800 via the bus 816.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. A method of identifying intraretinal fluid in optical coherence tomography (OCT) image data of an eye, said method comprising:
   (a) collecting OCT image data using an OCT system, said data including at least one cluster scan containing OCT image data collected at approximately same set of locations on the sample;
   (b) generating a first motion contrast image by applying a first OCT angiography processing technique to the cluster scan to highlight motion contrast in the sample;
   (c) generating a second motion contrast image by applying a second OCT angiography processing technique to the cluster scan to highlight motion contrast in the sample, wherein the first OCT angiography processing technique is different from the second OCT angiography processing technique;
   (d) generating an image displaying intraretinal fluid in the eye using the first and second motion contrast images; and
   (e) displaying or storing the image displaying intraretinal fluid or a further analysis thereof.

2. The method as recited in claim 1, wherein step (d) comprises:
   (d1) repeating steps (a)-(c) to generate a set of difference images over a range of transverse locations on the sample, in which a difference image is generated by comparing the first and second motion contrast images in each iteration;
   (d2) combining the difference images to create a three-dimensional (3D) volume of difference images; and
   (d3) generating a two-dimensional (2D) representation of the 3D volume of difference images that displays intraretinal fluid in the eye.

3. The method as recited in claim 1, in which the first OCT angiography processing technique is a high sensitivity OCT angiography processing technique and the second OCT angiography processing technique is a low sensitivity OCT angiography processing technique.

4. The method as recited in claim 3, in which the high sensitivity OCT angiography processing technique is a phase-related technique and the low sensitivity OCT angiography processing technique is an intensity-based technique.

5. A method to reduce the impact of artifacts in optical coherence tomography (OCT) angiography images of a sample, said method comprising:
   collecting OCT image data using an OCT system, in which the OCT image data includes at least one cluster scan containing data collected at approximately same set of locations on the sample;
   generating a first motion contrast image by applying a first OCT angiography processing technique to the OCT image data to highlight motion contrast in the sample;
   generating a second motion contrast image by applying a second OCT angiography processing technique to the OCT image data to highlight motion contrast in the sample, wherein the first OCT angiography processing technique is different from the second OCT angiography processing technique;
   generating an artifact reduced image using the first and second motion contrast images; and
   displaying or storing the artifact reduced image.

6. The method as recited in claim 5, wherein generating the artifact reduced image comprises:
   identifying locations of artifacts in the first motion contrast image;
   identifying the corresponding locations in the second motion contrast image; and
   replacing the data for the locations with artifacts in the first motion contrast image with the data from the corresponding locations in the second motion contrast image to create the artifact reduced image.

7. The method as recited in claim 6, further comprising adjusting the brightness of the replacement data to improve the quality of the artifact reduced image.

8. The method as recited in claim 6, in which identifying the locations of artifacts in the first motion contrast image is based on comparing the first and second motion contrast images.

9. The method as recited in claim 8, in which the comparison involves subtraction of the first and second motion contrast images.

10. The method as recited in claim 5, in which the OCT image data consists of a first set of OCT image data collected with a first set of imaging conditions and a second set of OCT image data collected with a second set of imaging conditions, wherein the first and second sets of imaging conditions are different.

11. The method as recited in claim 10, in which the first and second sets of OCT image data are three-dimensional volumes of OCT image data, and in which the second set of imaging conditions involves collecting the OCT image data along a different fast axis compared to the first set of imaging conditions.

12. The method as recited in claim 10, in which the first motion contrast image is generated by applying the first OCT angiography processing technique to the first set of OCT image data, and in which the second motion contrast image is generated by applying the second OCT angiography processing technique to second set of OCT image data.

13. The method as recited in claim 12, wherein generating the artifact reduced image comprises:
    identifying locations of differences between the first and second contrast images;
    removing the areas of differences in the first and second motion contrast images; and
    combining the first and second motion contrast images into a composite image.

14. The method as recited in claim 13, in which identifying the locations of differences between the first and second motion contrast images is based on comparing the first and second motion contrast images.

15. The method as recited in claim 13, further comprising:
    generating a third motion contrast image by applying a third OCT angiography processing technique to the first or the second set of OCT image data to highlight motion contrast in the sample;
    comparing the third motion contrast image to the composite image to identify locations of artifacts in the composite image;
    identifying the corresponding locations in the third motion contrast image;
    replacing the data for the locations with artifacts in the composite image with the data from the corresponding locations in the third motion contrast image to create an artifact reduced composite image; and
    displaying or storing the artifact reduced composite image.

16. The method as recited in claim 5, in which the first OCT angiography processing technique is a phase-related technique and the second OCT angiography processing technique is an intensity-based technique.

17. The method as recited in claim 16, in which the phase-related intensity technique is one of a correlation mapping OCT (cmOCT) technique, a speckle variance technique, an amplitude decorrelation technique, and a complex difference after log technique.

* * * * *

UNITED STATES PATENT AND TRADEMARK OFFICE
CERTIFICATE OF CORRECTION

PATENT NO. : 10,264,963 B2
APPLICATION NO. : 15/762045
DATED : April 23, 2019
INVENTOR(S) : Lin An et al.

It is certified that error appears in the above-identified patent and that said Letters Patent is hereby corrected as shown below:

In the Specification

Column 10, Line 3, delete "$\overline{(Dif)}$" and insert -- $\overline{(Dif)}$ --, therefor.

Column 10, Line 64, delete "avasculature" and insert -- avascular --, therefor.

Column 14, Line 12, after "31)" insert -- . --.

Signed and Sealed this
Eleventh Day of August, 2020

Andrei Iancu
*Director of the United States Patent and Trademark Office*